United States Patent [19]
Kirchhoff et al.

[11] Patent Number: 5,354,929
[45] Date of Patent: Oct. 11, 1994

[54] BISBENZOCYCLOBUTENE COMPOUNDS WITH HYDROPHOBIC SUBSTITUENTS, A METHOD FOR MAKING SAME

[75] Inventors: Robert A. Kirchhoff; P. J. Thomas; R. Garth Pews, all of Midland, Mich.

[73] Assignee: The Dow Chemical Company, Midland, Mich.

[21] Appl. No.: 128,611

[22] Filed: Sep. 28, 1993

[51] Int. Cl.$^5$ .............................................. C07C 13/00
[52] U.S. Cl. ....................................... 585/26; 585/24; 585/25; 528/396
[58] Field of Search ............................ 585/24, 25, 26; 528/396

[56] References Cited

U.S. PATENT DOCUMENTS

| | | | |
|---|---|---|---|
| 4,540,763 | 9/1985 | Kirchhoff | 526/281 |
| 4,812,588 | 3/1989 | Schrock | 556/453 |

FOREIGN PATENT DOCUMENTS 0227163  7/1987  European Pat. Off. .

OTHER PUBLICATIONS

"Benzocyclobutenes in Polymer Synthesis" by R. A. Kirchhoff et al. listed in Prog. Polym. Sci. vol. 18, 85–185, ©1993.

"Diketone Bis-Benzocyclobutene As a High Performance Matrix Resin" by K. J. Bruza et al. listed in 36th International SAMPE Symposium Apr. 15–18, 1991; pp. 457–468.

"Silane Reductions in Acidic Media. II. Reductions of Aryl Aldehydes and Ketones by Trialkylsilanes in Trifluoracetic Acid. A Selective Method for Converting the Carbonyl Group to Methylene" by Charles T. West et al. listed in Journal of Organic Chemistry, vol. 38, No. 15 1973; pp. 2675–2681.

"A Novel and Versatile Synthese of 1-arylbenzocyclobutenols and 1-arylbenzocyclobutenes" by Indrapal S. Aidhen et al. listed in Indian Journal of Chemistry vol. 32B, Feb. 1993 pp. 234–238.

"Cure Technology for Controlled Stress in Thin Benzocyclobutene Coatings" by P. H. Townsend et al. listed in Mat. Res. Soc. Symp. Proc. vol. 264 ©1992 Materials Research Soc. pp. 135–140.

"Reduction of Carbonyl Groups" by Owen H. Wheeler ©1966, Interscience Publishers, vol. 1 Chapter 11, pp. 507–566.

"Benzocyclobutenes: A New Class of High Performance Polymers" by R. A. Kirchhoff et al. in Journal of Macromolecular Science, ©1991 by Marcel Dekker, Inc., pp. 1094 and 1104–1106.

"Reduction of Carbonyl Groups" by Theophil Eicher, ©1966, Interscience Publishers, vol. 1 Chapter 13, pp. 621–693.

*Primary Examiner*—John Kight, III
*Assistant Examiner*—Terressa Mosley

[57] ABSTRACT

The invention is a bis-BCB compound of the structure:

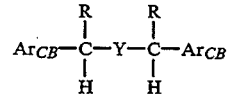

a method for making same and polymers made therefrom. The novel compounds of this invention are useful in preparing polymers that can form thin film coatings for multichip midules (MCMs) and integrated circuits (ICs). These compounds can be isolated as liquids at room temperature, and can form polymers that are hydrophobic and have low dielectrical and dissipative properties.

12 Claims, No Drawings

BISBENZOCYCLOBUTENE COMPOUNDS WITH HYDROPHOBIC SUBSTITUENTS, A METHOD FOR MAKING SAME

BACKGROUND OF INVENTION

This invention relates to bisbenzocyclobutene compounds (bisBCBs) containing hydrophobic substituents. An extensive review of benzocyclobutenes is Kirchhoff and Bruza's monograph "Benzocyclobutenes in Polymer Synthesis" (Prog. Polym. Sci., Vol 18, 85–185, 1993), herein incorporated by reference.

Polymers derived from benzocyclobutenes (BCBs) (of which bisBCBs are a subset) are described in U.S. Pat. No. 4,540,763. These polymers are prepared by subjecting BCBs to temperatures sufficient for polymerization. The polymers exhibit properties that make them useful for preparing composites, coatings, and films.

One useful property is a low dielectric constant. It is possible, as Kirchoff reports (pg 92 of the above-cited monograph), to prepare low dielectric constant hydrophobic benzocyclobutene polymers by starting with precursor monomers that contain hydrocarbon or siloxane groups interspersed between the reactive moieties of the monomer molecule. For example, the polymer of the divinylbenzene bisbenzocyclobutene compound shown below has a dielectric constant of 2.7.

Unfortunately, this compound has a melting point of 150°–152° C. which makes processing prior to polymerization time-consuming and costly.

Schrock addressed this deficiency in the art (U.S. Pat. No. 4,812,588) by preparing the liquid, tetramethyldivinyldisiloxane bisbenzocyclobutene (DVS-bisBCB), which is represented by the following structure:

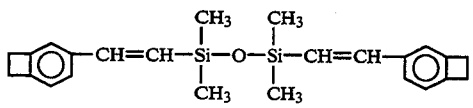

The polymer formed from DVS-bisBCB, poly-DVS-bisBCB has a low dielectric constant (2.55 at 1 MHz) a low dissipation factor (0.0008 at 1 MHz and <0.002 at 10 GHz), and low water absorption (0.25% at 100° C. for 24 hours). (See Kirchhoff et al., J. Macromol. Sci.-Chem., A28(1&12), pp. 1094 and 1104–1106.) Thus, poly-DVS-bisBCB is especially electrically resistive and hydrophobic.

One disadvantage of DVS-bisBCB is that it is not isolated as a single compound, but rather as a complex mixture of compounds. Since the composition of this mixture may vary from batch to batch, the nature of the polymer derived from the DVS-bisBCB monomer may also vary. Thus, there is a potential problem of variability in the properties of the polymer.

In view of the deficiency in the art, it would be desirable to have bisbenzocyclobutene compounds that were liquids at room temperature. At the same time, it is essential that the same desirable properties of the prior art polymers—low dielectric constants, low dissipation factors, and low water uptake—not be compromised.

SUMMARY OF INVENTION

The invention is a compound represented by:

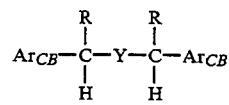

wherein:

Y is a divalent alkyl, cycloaliphatic, aromatic, heteroaromatic, or heterocyclic moiety;

each ArCB is an arylcyclobutene moiety attached to the adjacent —CHRY group through an atom on the aryl ring;

each R is independently hydrogen, or inertly substituted alkyl, cycloalkyl, or aryl.

An inert substituent is one that is unreactive in a subsequent polymerization process. Arylcyclobutenes are represented by the following structure:

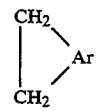

wherein Ar is aromatic with the proviso that the $CH_2$ groups are bonded to adjacent carbons on the same aromatic ring of Ar.

The invention is also a process for preparing the above-represented compound.

The novel compounds of this invention are useful in preparing polymers that can form thin film coatings for multichip midules (MCMs) and integrated circuits (ICs). These compounds can be isolated as liquids at room temperature, and can form polymers that are hydrophobic and have low dielectrical and dissipative properties.

A further aspect of this invention is the polymerized product formed from the above-represented compound.

DETAILED DESCRIPTION OF INVENTION

The compounds of this invention can be prepared by starting with a diketone (I) represented by the following structure:

where Y is a divalent alkyl, cycloaliphatic, aromatic, heteroaromatic, or heterocyclic moiety; and each ArCB is an arylcyclobutene moiety attached to the adjacent carbonyl group through an atom on an aromatic ring of the arylcyclobutene moiety.

Y is preferably arylene or an unsubstituted arylene group such as phenylene, naphthylene, anthrylene, or phenanthrylene; more preferably, Y is phenylene; and most preferably, Y is 1,3-disubstituted phenylene.

Preferably, Ar$_{CB}$ is a benzocyclobutenyl group. (Note: the term benzocyclobutenyl is used to refer to a monosubstituted benzocyclobutene, i.e., a monosubstituted bicyclo[4.2.0]octa-1,3,5-triene. This usage is consistent with that of Kirchhoff and Bruza, "Benzocyclobutenes in Polymer Synthesis", supra.) More preferably, ArCB is a benzocyclobutenyl group and Y is 1,3-diphenylene. The most preferred diketone is 1,3- phenylenebis[bicyclo-(4.2.0)octa-1,3,5-trien-3-yl](diketone bisbenzocyclobutene or DK-bisBCB), the synthesis of which is described in Bruza et al., Proc. 36th Int. Sampe Symp. 458 (1991), incorporated herein by reference.

The diketone (I) is first reacted with a first reducing agent to form a substituted or unsubstituted diol represented by the following structure:

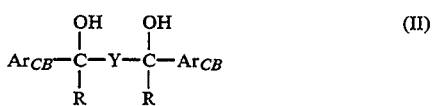 (II)

where R is hydrogen, or an inertly substituted aryl, alkyl, or cycloalkyl group.

The first reducing agent is an agent that reduces the the carbonyl carbon atom to a secondary or tertiary alcohol, but does not otherwise undesirably react with the diketone (I).

For the case where R is H, the first reducing agent can be catalytic hydrogenation, wherein a preferred catalyst is palladium over a carbon support. Alternatively, the reducing agent can be $NaBH_4$. For a general review of the reduction of carbonyl groups, including reduction by catalytic hydrogenation and $NaBH_4$, see Wheeler in Patai, "The Chemistry of the Carbonyl Group," vol. 1, pp. 507–566, Interscience Publishers, New York, 1966, incorporated herein by reference.

Again where R is H, it is further possible to reduce the diketone directly to the compound of the invention using a trialkylsilane in a trifluoroacetic acid medium. In general, two equivalents of trialkylsilane are required for the reduction of one equivalent of carbonyl compound to the methylene product. For examples of a one-step reduction of ketones to alkanes using trialkylsilanes in trifluoroacetic acid media, see West et al., Journal of Organic Chemistry, 38, (1973), 2675, incorporated herein by reference.

Where R is inertly substituted alkyl, cycloalkyl, or aryl, the first reducing agent can be RLi. More preferably, the first reducing agent is a Grignard reagent RMgX, where X is halogen, and preferably chloride or bromide. For a general review of the addition of organometallic compounds to carbonyl groups, see Eicher in Patai, supra, pp 621–693.

Theoretically, two moles of Grignard reagent are required to reduce one mole of the diketone to the corresponding diol. In practice, the Grignard reagent is advantageously used in stoichiometric excess so that the diketone is the limiting reagent. The preferred Grignard reagents are phenylMgCl, phenylMgBr, methylMgCl, methylMgBr, tolylMgBr, and tolylMgCl. The more preferred Grignard reagents are phenylMgCl and phenylMgBr.

A Grignard reagent-solvent mixture is advantageously added to a stirred solution of the diketone (I) at a rate and a temperature appropriate to control the resultant exotherm and minimize the formation of side products. Suitable such temperatures are subambient, preferably from between about $-10°$ C. to about $0°$ C. The reaction is carried out under substantially moisture-free and oxygen-free conditions to prevent side reactions of the Grignard reagent with air or moisture.

When the addition of the Grignard reagent to the diketone (I) is complete, the temperature of the reaction mixture may be adjusted to enhance the rate of reaction. Stirring is generally continued until the reaction is substantially complete.

The intermediate product of the Grignard reaction is a dimagnesium salt. This salt is hydrolyzed to the corresponding diol (II) with dilute aqueous acid, preferably dilute hydrochloric or sulfuric acid. The more preferred hydrolyzing reagent is aqueous ammonium chloride, preferably a saturated solution of ammonium chloride.

After hydrolysis, the diol (II) can be isolated by extraction with an organic solvent that dissolves the diol (II) but that is immiscible with the inorganics, such as methylene chloride. Residual acids and salts can be removed from the organic extract, typically by water washing. Any residual water can be substantially removed from the organic extract by a drying reagent, such as anhydrous magnesium sulfate. The diol (II) can generally be used without further purification for the second reduction reaction.

The preferred diol is represented by the following structure:

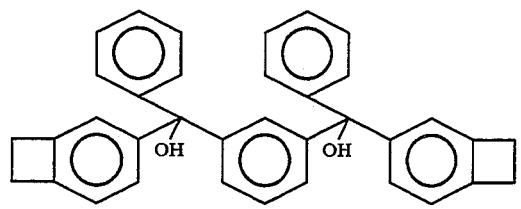

In the second step of the reaction, the diol (II) is reacted with a second reducing agent to form a compound having the following structure:

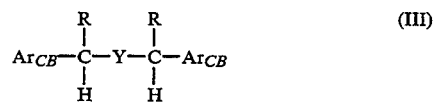 (III)

The second reducing agent is one that reduces an alcohol to a methine moiety. Exceptionally, where R is hydrogen, the alcohol is reduced to a methylene moiety. The second reducing agent can be, for example, hydrogen over a catalyst, $LiAlH_4$, $NaBH_4$, or an organosilane in a protic acid medium, wherein the protic acid is soluble with the organosilane, but does not react therewith. Preferably, the second reducing agent is an organosilane in a protic acid medium, more preferably, an organic protic acid medium. More preferably, the reducing agent is triethyl silane in a trifluoroacetic acid medium. This means of reducing alcohols to alkanes is known. For examples of reduction by triethylsilane-trifluoroacetic acid, see West et al., supra; and Aidhen et al., Indian Journal of Chemistry, Vol. 32B, (1993), 234; incorporated herein by reference.

In the most preferred mode of the second reduction reaction, the diol (II) is combined and stirred in a reactor with trifluoroacetic acid and a nonhydroxylic solvent, such as methylene chloride. These solvents can be to moderate the reaction temperature during the the addition of triethylsilane, or to facilitate the homogeneity of the solution. (See West et al., supra, page 2676.) Triethylsilane is then added in such manner as to control the resultant exotherm as well as the formation of side products. Alternatively, triethylsilane can be added in combination with a solvent, such as methylene chloride.

Alternatively, the diol (II) can be combined with triethylsilane in the reactor and trifluoroacetic acid added separately. In either case, trifluoroacetic acid is usually, but not always, used in molar excess of the triethylsilane. Triethylsilane is generally used in stoichiometric excess of the diol (II), so that the latter is the limiting reagent in the reaction. The temperature of the reaction mixture is generally maintained at or below room temperature, and preferably between about 0° C. to about 10° C.

Upon completion of the combining of the triethylsilane, trifluoroacetic acid and the diol, the temperature of the mixture can be adjusted to enhance the reaction rate. In a preferred mode, the temperature is raised from between about 0° C. and about 10° C. to about ambient temperatures. Stirring of the mixture is advantageously continued until the reaction is substantially complete. Volatile components of the mixture can then be substantially removed, typically in vacuo, and the remaining mixture can be combined with water.

An organic solvent, advantageously selected to dissolve the product (III) and to be immiscible with water, such as methylene chloride, can be used to extract the product of the reaction mixture. Once the organic extract is isolated, it can be washed, then dried over a drying agent such as magnesium sulfate. The compound can be purified by means such as flash chromatography or vacuum distillation.

An alternative to extracting the desired product with an organic solvent after substantial removal of all volatile components is to purify without extraction by means such as column chromatography or vacuum distillation.

The final product of the previous reaction is the compound of the invention, represented by the structure:

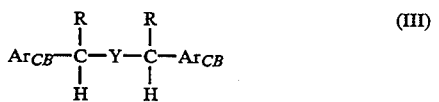

(III)

where:

Y is a divalent alkyl, cycloaliphatic, aromatic, heteroaromatic, or heterocyclic moiety; and each ArCB is an arylcyclobutene moiety attached to the adjacent —CHRY group through an atom on an aromatic ring of the arylcyclobutene moiety;

Y is preferably arylene or an unsubstituted arylene group such as phenylene, naphthylene, anthrylene, or phenanthrylene; more preferably, Y is phenylene; and most preferably, Y is 1,3-disubstituted phenylene;

$Ar_{CB}$ is preferably a benzocyclobutenyl group; more preferably, $Ar_{CB}$ is a benzocyclobutenyl group and Y is 1,3-diphenylene;

R is hydrogen, or inertly substituted aryl alkyl, or cycloalkyl; preferably R is inertly substituted aryl or alkyl; more preferably R is methyl, phenyl, or tolyl; more preferably, R is phenyl; and most preferably, $Ar_{CB}$ is a benzocyclobutenyl group, Y is 1,3-diphenylene, and R is phenyl.

The most preferred compound of the second reduction reaction is trityl-bisBCB, represented by the following structure:

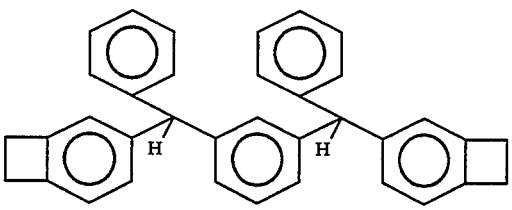

(IV)

Surprisingly, trityl-bisBCB is obtained as a viscous liquid at room temperature using the conditions outlined in Example 1, at a purity of greater than 90%, preferably greater than 95%, more preferably greater than 97%. (Because trityl-bisBCB has two chiral centers and a plane of symmetry therebetween, it is believed to be a combination of stereoisomers—a d,l pair and a meso form. Thus, a 97% pure trityl-bisBCB means that the combination of the stereoisomers comprises 97% of the compound.) The fact that trityl-bisBCB is a liquid at room temperature at purities greater than 90% desirably distinguishes it from most bisBCB compounds, which are solids at room temperature. As a liquid, trityl-bisBCB is readily processable to thin film insulating polymeric coatings for MCMs and ICs.

Polymerization Reactions

A polymer is formed from the compound (III) by subjecting the compound (III) to conditions suitable for polymerization. A teaching of the various polymerizations of BCBs can be found in U.S. Pat. No. 4,540,763, page 20, line 20 through page 22. In general, the polymerization (or curing) process is a thermal one, and useful polymers can be prepared using a wide range of temperatures and reaction times. For example, a BCB compound can be cured at 350° C. in minutes or at 150° C. in 10 days and in either case will produce a polymer that is useful for certain applications.

The following discussion will focus on the process for creating melt polymerized thin films on a substrate as well as bulk polymers from the compound (III) of this invention. In general, differential contraction between a thin film polymer and a substrate commonly used in MCM or IC applications, such as silicon or alumina, can lead to film stress, which in turn can lead to undesirable wafer bow or film fracture. Thus, the polymerization process is carried out in such a way as to form films that have a minimal amount of stress, as well as films that are substantially free of flaws; that is, free of cracks, bubbles, and voids.

In one embodiment of the polymerization reaction, the compound (III) is first devolatilized. This devolatilization can be accomplished by heating the compound (III) under ambient or reduced pressure, to a contacting temperature that is sufficiently low to prevent onset of polymerization over the course of the devolatilization process, yet sufficiently high to devolatilize the compound (III). Typically, this contacting temperature is from about 80° C. to about 200° C., preferably from about 80° C. to about 160° C., more preferably from about 150° C. to about 160° C.

After the compound (III) is substantially 0 devolatilized, it can be returned to ambient pressure (if not already at ambient pressure) and maintained at the devolatilization contacting temperature. Then, the contacting temperature can be ramped to initiate formation of a higher average molecular weight entity, or prepolymer. This contacting temperature is advantageously ramped at such a rate that the glass transition temperature ($T_g$) of the prepolymer, which increases as the contacting temperature is increased, always exceeds that of the contacting temperature throughout the polymerization process. The $T_g$ of the prepolymer (as measured by, for example, dynamic scanning calorimetry or dynamic mechanical spectrometry) increases with time and increasing temperature because the average molecular weight of this entity increases with time and increasing temperature. Preferably, the contacting temperature is ramped at the rate of between about 0.01C.°/min and about 200 C.°/min, more preferably between about 0.05 C.°/min and about 5 C.°/min, most preferably between about 0.05 C.°/min and 2 C.°/min; to between about 170° C. and about 220° C., more preferably between about 190° C. and about 200° C; preferably for at least 1 hour, more preferably for between about 2 and about 24 hours, to form the prepolymer.

Then, the prepolymer is ramped at the rate of between about 0.01C.°/min and about 200 C.°/min, more preferably between about 0.05 C.°/min and about 5 C.°/min, most preferably between about 0.05 C.°/min and 2 C.°/min; to between about 220° C. and about 300° C., more preferably, between about 240° C. and about 260° C., for a time sufficient to cure the polymer, preferably for between about 10 minutes and about 3 hours.

The substantially cured polymer is then cooled to room temperature at a rate that minimizes stress, preferably between about 0.01C.°/min and about 200 C.°/min, more preferably between about 0.05 C.°/min and about 5 C.°/min, most preferably between about 0.05 C.°/min and 1 C.°/min.

Melt polymerization is carried out as described above so that the resultant polymeric film exerts a compressive stress on its substrate upon heating. Thus, when the polymer is substantially cured, then cooled, the film contracts, and develops a minimal amount of stress in tension.

On the other hand, when the contacting temperature is ramped so as to equal or exceed the $T_g$ of the compound, the resultant polymeric film expands undesirably in a fluid-like state while it cures on its substrate. When a film cured in this manner is cooled, the differential contraction between the film and the substrate is such that the resultant film stress in tension in undesirably higher. For a discussion on controlling stress in BCB coatings, see Townsend et al., "Cure Technology for Controlled Stress in Thin Benzocyclobutene Coatings" MRS Symposium Proceedings, San Francisco, April 1992, incorporated herein by reference.

In a second polymerization process, a substantially flawless polymer can be made by heating the compound (III) under pressure. Apparently, high pressures prevent outgassing of volatiles, which may be present and which may cause of bubble formation. Secondly, high pressures suppress the formation of voids in the polymer.

For example, the compound (III) is heated to between about 80° C. and about 200° C., poured into a mold, then subjected to pressures between about 100 and about 2000 psi. Thereafter, compound (III) is heated to between about 200° C. and about 300° C., more preferably between about 200° C. and about 250° C., for between about 10 minutes and about 3 hours. Upon cooling, the polymerized composition can be removed from the mold. This process is described in U.S. Pat. No. 4,540,763, supra.

The preferred polymer, poly-trityl-bisBCB has a dielectric constant of 2.68 at 500 KHz, and a dissipation factor of 0.00034. Measurements of these properties were made in accordance with ASTM Designation: CD 150-87, Standard Test Methods for AC Loss Characteristics and Permittivity (Dielectric Constant) of Solid Electrical Insulating Materials, November, 1987.

EXAMPLE 1

Preparation of Trityl-BisBCB

To a stirred solution of 20 g (0.06 mol) of DK-bisBCB in 120 mL of dry tetrahydrofuran under nitrogen atmosphere at 0°-10° C., is added 90 mL of 2M solution of phenyl magnesium chloride in tetrahydrofuran (0.18 mol active ingredient) over a period of 20 minutes. The reaction mixture is slowly warmed to room temperature, stirred for 5 hours and poured into 200 mL of saturated ammonium chloride solution. The mixture is extracted with methylene chloride, and the organic layer washed with water and dried over anhydrous magnesium sulfate. Removal of the solvent gives 32 g of a crude diol which is used without further purification in the next step.

To a stirred solution of the diol and trifluoroacetic acid (150 mL) in 150 mL of methylene chloride at 0°-10° C., is added 44 mL of triethylsilane (0.28 mol) dropwise over a period of 20 minutes. The mixture is slowly warmed to room temperature and stirred for 2 hours. Excess trifluoracetic acid is removed by rotary evaporation and poured into 200 mL of water. The mixture is extracted with methylene chloride, and the organic layer washed with water, then sodium bicarbonate solution, then brine. Drying and removal of the solvent followed by purification by flash chromatography using hexanes as the eluent affords 15 g (55% overall yield) of trityl-bisBCB. The purity (the combination of the trityl-bisBCB stereoisomers) is determined to be greater than 98% by high performance liquid chromatography.

EXAMPLE 2

Preparation of Poly-Trityl BisBCB

A sample of trityl-bisBCB is placed in a beaker and transferred to a vacuum oven heated at 160° C. The pressure is reduced to 1" of Hg and the sample degassed for 1 hour. The vacuum is released and the molten monomer poured into a mold preheated to 160° C., which is then placed in an oven at 160° C. The temperature of the oven is then raised at 1 C.°/minute to 190° C. The mold is then held at 190° C. for 16 hours, after which time it is heated at 1 C.°/minute to 250° C. The mold is then held at 250° C. for 1 hour, and finally cooled down to room temperature at 0.1 C.°/minute.

What is claimed is:

1. A compound represented by:

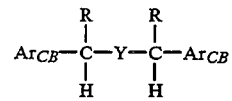

wherein:
Y is a divalent alkyl, cycloaliphatic, aromatic, heteroaromatlc, or heterocyclic moiety;
each $Ar_{CB}$ is an arylcyclobutene moiety attached to the adjacent —CHRY group through an atom on the aromatic ring;

each R is independently selected from the group consisting of inertly substituted alkyl, cycloalkyl, and aryl.

2. The compound of claim 1 wherein Y is selected from the group consisting of phenylene, naphthylene, anthrylene, and phenanthrylene.

3. The compound of claim 2 wherein Y is phenylene.

4. The compound of claim 3 wherein R is phenyl.

5. The compound of claim 4 represented by:

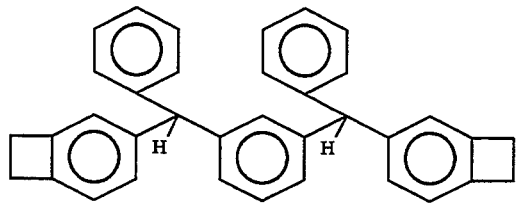

(IV)

6. A method comprising the steps of a) reacting a diketone having the structures:

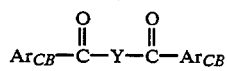

with a first reducing agent to form a diol having the structure:

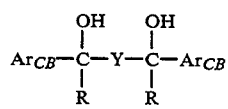

wherein:
each R is selected from the group consisting of hydrogen, inertly substituted alkyl, inertly substituted cycloalkyl, and inertly substituted aryl;
Y is a divalent alkyl, cycloaliphatic, aromatic, heteroaromatic, or heterocyclic moiety; and
each ArCB is an arylcyclobutene moiety attached to the adjacent carbinol group through an atom on the aromatic ring; then b) reacting the diol with a second reducing means to form having the structure:

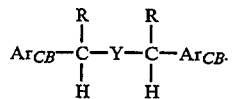

7. The method of claim 6 wherein the first reducing agent is RMgCl or RMgBr, R being selected from the group consisting of inertly substituted alkyl, inertly substituted cycloalkyl, and inertly substituted aryl.

8. The method of claim 6 wherein the first reducing agent is triethylsilane in trifluoroacetic acid.

9. The method of claim 7 wherein R is phenyl.

10. The method of claim 9 wherein the diketone is diketone bisbenzocyclobutene.

11. The method of claim 10 wherein the second reducing agent is a silane in conjunction with a protic acid.

12. The method of claim 11 wherein the silane is triethylsilane and the protic acid is trifluoroacetic acid.

* * * * *

UNITED STATES PATENT AND TRADEMARK OFFICE
CERTIFICATE OF CORRECTION

PATENT NO. : 5,354,929
DATED : Oct. 11, 1994
INVENTOR(S) : R. A. Kirchhoff, P. J. Thomas, and R. G. Pews.

It is certified that error appears in the above-indentified patent and that said Letters Patent is hereby corrected as shown below:

Col. 8, line 65, "heteroaromatlc" should read -- heteroaromatic --.

Col. 9, line 29, "structures" should read -- structure --.

Col. 10, line 17, insert -- a compound -- after "form".

Signed and Sealed this

Twenty-fourth Day of October, 1995

Attest:

BRUCE LEHMAN

Attesting Officer

Commissioner of Patents and Trademarks